United States Patent [19]
Holzner et al.

[11] Patent Number: 5,565,615
[45] Date of Patent: Oct. 15, 1996

[54] METHOD OF PREPARING DIMETHYLAMINE-BORANE

[75] Inventors: Christoph Holzner, Köln; Alfred Wagner, Leverkusen; Dietrich Pantke, Ratingen; Hans-Dieter Block, Leverkusen; Hans-Heinrich Moretto, Leverkusen; Wolfgang Ohlendorf, Leverkusen, all of Germany

[73] Assignee: Bayer Aktiengesellschaft, Leverkusen, Germany

[21] Appl. No.: 413,681

[22] Filed: Mar. 30, 1995

[30] Foreign Application Priority Data

Apr. 6, 1994 [DE] Germany .......................... 44 11 752.3

[51] Int. Cl.⁶ ...................................... C07F 5/02
[52] U.S. Cl. ...................................... 564/9; 564/8
[58] Field of Search ................................ 564/8, 9

[56] References Cited

U.S. PATENT DOCUMENTS 4,709,083  11/1987  Spielvogel ................... 564/9

FOREIGN PATENT DOCUMENTS 1178077   7/1964   Germany .
1618387   12/1970  Germany .
60-149593 8/1985   Japan .......................... 564/9
826558    2/1956   United Kingdom .

OTHER PUBLICATIONS

Y. Kikugona, Chem. Pharm Bull. vol. 35, pp. 4988–4989 (1987).
North et al. Chemische Berichte, vol. 3, pp. 928–938 (1960).
Derwent Abstract of JP 60-149,593 (Jan. 12, 1989).
Hawthorne, JACS, 2671–2673, 1961.

*Primary Examiner*—Shailendra Kumar
*Attorney, Agent, or Firm*—Sprung Horn Kramer & Woods

[57] ABSTRACT

In the preparation of dimethylamine-borane by reacting an alkali metal or alkaline earth metal borohydride with a dimethylammonium salt, the improvement which comprises effecting the reaction in a liquid mixture comprising dimethylamine as a solvent and an additional organic solvent.

13 Claims, No Drawings

METHOD OF PREPARING DIMETHYLAMINE-BORANE

The present invention relates to a method of preparing dimethylamine-borane ($(CH_3)_2NHBH_3$) by the reaction of a borohydride with a dimethylammonium salt.

Dimethylamine-borane has diverse applications in the art. Thus it is used as a reducing agent for the chemical deposition of metals on non-conducting materials, as a selective reducing agent in organic synthesis, and as a stabilizer for organic products. According to the prior art, dimethylamine-borane is prepared from an alkali metal or alkaline earth metal borohydride and a dimethylammonium salt in a solvent or reaction medium.

The selection of the solvent or of the reaction medium is critical for this reaction. Water (DE-OS 1 618 387) or liquid ammonia (DE-AS 1 178 077) have a very good dissolving power for borohydride and dimethylammonium chloride educts. However, water has the disadvantage that significant losses of yield occur due to the hydrolysis of the $BH_3$ formed as an intermediate. Liquid ammonia necessitates working at very low temperatures or at an elevated pressure, on account of its low boiling point of $-33°$ C.

Organic solvents in general have a reduced dissolving power for educts compared to $H_2O$ or $NH_3$, so that the reactants are only partially dissolved and have to be used in suspension. Polar, aprotic solvents have hitherto been used, such as ethylene glycol dimethyl ether (JP 60 149 593 of 7.8.85), diethyl ether, tetrahydrofurane (H. Nöth, H. Beyer, Chemische Berichte, Volume 3, 1960, pages 928 to 938) or dimethylformamide (JP 560 054 90 of 20.1.91; CA 95 (9): 80115 r). Because of their polar nature, solvents such as these are not capable of dissolving sufficient borohydride and dimethylammonium salt and are thus not capable of facilitating a sufficiently rapid and complete reaction.

However the use of ethers such as diethyl ether, tetrahydrofurane or ethylene glycol dimethyl ether in the art is highly problematical, since these tend to form explosive peroxides. Ethylene glycol dimethyl ether, which also gives the best results of the aforementioned ethers (Y. Kikugawa; Chem. Pharm. Bull., Volume 35, 1987, pages 4988 to 4989) has the additional disadvantage of a very high price, so that its use as a solvent is disadvantageous. Moreover, this water-soluble ether makes it impossible to work up the reaction mixture by extraction with water, which is why filtration has been established as the only possible operation for separating the by-products from dimethylaminoborane.

Dimethylformamide, which also is water-soluble, has the additional disadvantage that it is not easily volatilized, so that after filtration it cannot be completely separated by simple distillation from the dimethylamine-borane reaction product dissolved therein (Y. Kikugawa, ibid).

The object of the present invention is therefore to provide a method of preparing dimethylamine-borane in which the desired product is obtained in high yield and purity without expensive purification steps, using inexpensive and easily handled starting materials.

This object can be achieved by means of the method according to the invention.

The present invention relates to a method of preparing dimethylamine-borane by the reaction of an alkali metal or alkaline earth metal borohydride with a dimethylammonium salt, which is characterized in that the reaction is conducted in a liquid mixture of dimethylamine and an organic solvent.

Li, Na, K, Mg and Ca ions, for example, are particularly suitable alkali metal or alkaline earth metal ions for the borohydride used, Na ions being particularly preferred.

The dimethylammonium salt may be produced in situ by the addition of an anhydrous acid to the liquid mixture (to the dimethylamine), or may be used in solid form for the reaction.

Mineral acids such as hydrogen halides and sulphuric acid, or carboxylic acids, such as HCl, HCOOH, $CH_3COOH$, $C_2H_5COOH$, etc., for example, may be used as the anhydrous acids. The dimethylammonium salt is then also present as the corresponding salt.

The borohydride and the dimethylammonium salt are preferably used as pure solids in the reaction mixture. However, the dimethylammonium salt may be produced in situ by the addition of an anhydrous acid to the reaction mixture, since the dimethylamine used as the solvent component is present in large excess with respect to the acid or borohydride during the reaction. The separate preparation of dimethylammonium salts which cannot be purchased can then be dispensed with.

In addition to dimethylamine an additional organic solvent is used, preferably from the group comprising hydrocarbons, ethers and carboxylic acid esters, such as toluene, diethyl ether, ethyl acetate, etc., for example.

Sodium borohydride and dimethylammonium sulphate and acetate are particularly preferred.

A solvent from the group comprising ethers or carboxylic acid esters is preferably used for the reaction of $NaBH_4$ with dimethylammonium sulphate. A solvent from the hydrocarbon group is preferably used for the reaction of $NaBH_4$ with dimethylammonium acetate.

Liquid dimethylamine has not previously been used as a solvent for the preparation of dimethylamine-borane from a borohydride and a dimethylammonium salt.

This is because one skilled in the art is also aware from the literature that "when liquid organic amines are used, the reaction only proceeds satisfactorily if both reactants are soluble in the amines" (DE-AS 1 178 077, column 1, lines 26 to 29). The solubility of sodium borohydride in liquid dimethylamine (boiling point 7° C.) at 2° C. is also given as only 4% (GB-PS 826 558, page 1, lines 53 to 55). Only amines with higher boiling points, such as pyridine or morpholine, have been used as the solvent for the reaction of sodium borohydride with the corresponding ammonium salt at elevated temperature for the synthesis of the corresponding borane (Gmelin Handbuch der Organischen Chemie, Eighth Edition, Volume 45, Part 14, pages 73 and 121).

It is just as surprising that hydrocarbons such as toluene can also be used as the solvent, since although they are very inexpensive and easy to handle, they belong to the group comprising very non-polar solvents.

After mixing together all the starting materials, the volumetric ratio of dimethylamine to solvent is preferably 1:10 to 3:1, most preferably 1:1 to 1:3.

Due to its low boiling point, pure dimethylamine results in only a very slow and incomplete reaction of $NaBH_4$ with the dimethylammonium salt.

In pure toluene, either no reaction occurs or the reaction proceeds only very slowly and incompletely.

It is all the more surprising that in a reaction mixture comprising liquid and toluene, for example, yields of dimethylamine-borane of >80% theoretical can be obtained after a reaction time of 2 to 3 hours (see Examples 1 and 3).

The sequence in which the components are added is arbitrary as long as a solid dimethylammonium salt is used as the educt. If the dimethylammonium salt is produced in situ during the reaction by the addition of acid, the sequence is no longer arbitrary. It is advantageous to produce the dimethylammonium salt in the absence of borohydride, whereupon contact of the acid-sensitive borohydride with the acid is avoided. Very complete reaction and high reaction rates are obtained, for example, when the dimethylamine, organic solvent and acid are mixed together and the borohydride is added subsequently.

The foaming which sets in with hydrogen evolution can have an adverse effect on the reaction mixture.

This foaming can be prevented, for example, by changing the sequence of addition of the components: the borohydride is introduced into dimethylamine and the acid is slowly added to the solvent with intensive stirring. Decomposition of the borohydride due to the acid does not occur. Moreover the yields obtained are as good as in the aforementioned case.

Antifoaming agents may also be added as auxiliary materials to prevent the formation of foam. Suitable antifoaming agents comprise salts of alkylsulphuric acids, alkanesulphonic acids and their fluorinated alkyl derivatives, for example.

The temperature during the reaction is preferably between 0° C. and 40° C., most preferably between 10° C. and 30° C.

Completion of the reaction may be followed by a work-up stage, which can be varied within wide limits. Dimethylamine and the solvent can be separated and recovered by distillation and re-used in the preparation process. The salt formed can be separated from the dimethylamine-borane by filtration or by extraction.

For example, the dimethylamine-borane is preferably distilled off from the reaction mixture at atmospheric pressure or under reduced pressure. The remaining reaction mixture is cooled and freed from salt by filtration. The filtrate is freed from solvent at elevated temperature and under vacuum. Pure dimethylamine-borane remains as the residue.

In contrast to previously known comparable methods (Y. Kikugawa; Chem. Pharm. Bull. Volume 35, 1987, pages 4988 to 4988) additional purification steps such as recrystallization are unnecessary, since both the salt and any unreacted educts are completely removed on filtration.

When using a water-insoluble solvent, such as toluene for example, separation of the salt (residue) may also be effected by extraction with water. After the removal of the dimethylamine, the reaction mixture is intensively and thoroughly mixed for this purpose with water or with a salt solution which is as concentrated as possible, such as an $Na_2CO_3$ or NaCl solution for example. After phase separation the organic phase is freed from the water-insoluble solvent at an elevated temperature and preferably under vacuum. Pure dimethylamine-borane remains as the residue.

The claimed method of preparing dimethylamine-borane can also of course be applied to the preparation of other amine-boranes, wherein primary, secondary and tertiary amines may be present as the amine in the amine-borane. These amines may comprise acyclic, cyclic, bicyclic and polycyclic substituents, wherein the latter three groups include both isocyclic and heterocyclic substituents. The nitrogen atom of the amine itself may also occur as a ring atom of a cyclic, bicyclic or polycyclic compound, wherein other elements such as oxygen or sulphur may be present as further ring atoms in addition to carbon. A mixture of the respective amine and an organic solvent is similarly used as the reaction medium for the preparation of these amine-boranes, wherein a salt of the amine—either added as such or produced in situ by the addition of an acid—is reacted with a borohydride.

The invention will be described in more detail with reference to the following examples.

EXAMPLE 1

8.15 g (0.1 mole) dimethylammonium chloride were suspended in 60 ml dimethylamine at 0° C. 3.8 g (0.1 mole) sodium borohydride were then added. The suspension was heated to the reflux temperature (9° C.) with stirring. After 30 minutes 20 g toluene were added, due to which the reflux temperature increased to 15° C. The end of the reaction was discernible after 2.5 hours due to the fall-off in hydrogen evolution. Thereafter dimethylamine was distilled off by heating to 30° C. The residual dimethylamine was expelled with nitrogen after adding a further 20 ml toluene. The suspension was then stirred with water, whereupon the solids dissolved in the aqueous phase. The toluene phase was concentrated under vacuum (14 mbar) at temperatures up to a maximum of 80° C.

4.8 g pure dimethylamine-borane remained as the residue (81.5% theoretical yield: content (iodometric): 97.2%).

EXAMPLE 2

3.8 g (0.1 mole) sodium borohydride were suspended in 60 ml dimethylamine at 0° C. A solution of 5.0 g (0.05 mole) of sulphuric acid (98%) in 100 ml ethylene glycol dimethyl ether was then added drop-wise over 15 minutes with cooling. During the addition of the acid, the temperature of the reaction mixture increased to 22° C. A further increase to 29° C. was observed until the reaction was complete. Dimethylamine was boiled under reflux for the whole of this period.

The reaction was complete after 2 hours. Dimethylamine was distilled off from the suspension by heating to 60° C., the suspension was filtered and the filtrate was concentrated. 5.2 g dimethylamine-borane remained as the residue (88.3% theoretical).

EXAMPLE 3

19 g (0.5 mole) sodium borohydride were suspended in 93 ml dimethylamine and heated to the reflux temperature (9° C.). A solution of 30 g (0.5 mole) of acetic acid in 90 ml toluene was then added drop-wise over 1 hour with stirring. After a total period of two hours the temperature of the reaction mixture had increased to 30° C. and the reaction was complete. 45 ml dimethylamine were distilled off by heating to 70° C. The suspension was then cooled to −10° C. and filtered. After concentrating the filtrate, 29 g dimethylamine-borane were obtained (98% theoretical).

It will be understood that the specification and examples are illustrative but not limitative of the present invention and that other embodiments within the spirit and scope of the invention will suggest themselves to those skilled in the art.

We claim:

1. In the preparation of dimethylamine-borane by reacting an alkali metal or alkaline earth metal borohydride with a dimethylammonium salt, the improvement which comprises effecting the reaction in a liquid mixture comprising dimethylamine as a solvent and an additional organic solvent.

2. The method according to claim 1, wherein the dimethylammonium salt is produced in situ by the addition of an anhydrous acid to the liquid mixture.

3. The method according to claim 1, wherein hydrogen halide, sulphuric acid or a carboxylic acid is used as the anhydrous acid.

4. The method according to claim 1, wherein the dimethylammonium salt is added in solid form to the liquid mixture.

5. The method according to claim 1, wherein the organic solvent comprises a hydrocarbon, an ether or a carboxylic acid ester.

6. The method according to claim 2, wherein sodium borohydride is introduced into liquid dimethylamine and thereafter a solution of the anhydrous acid is added to the organic solvent.

7. The method according to claim 2, wherein a hydrogen halide or sulphuric acid is used as the anhydrous acid and an ether is used as the organic solvent.

8. The method according to claim 2, wherein a carboxylic acid is used as the anhydrous acid and a hydrocarbon is used as the organic solvent.

9. The method according to claim 2, wherein the salt is produced by addition of a solution of acetic acid in toluene.

10. The method according to claim 1, wherein solid dimethylammonium chloride and toluene are used.

11. The method according to claim 1, wherein the reaction is effected at a temperature of about 0° C. to 40° C.

12. The method according to claim 1, wherein the liquid solvent contains an antifoaming agent selected from the group consisting of an alkyl sulphate, alkane sulphonate or a fluorinated alkyl derivative thereof in the form of its salt.

13. The method according to claim 1, including the further steps of separating dimethylamine and the organic solvent by distillation and separating remaining dimethylamine-borane from by-products and unreacted educts by filtration or by extraction with water or an aqueous salt solution.

* * * * *